United States Patent
Keller et al.

(10) Patent No.: US 6,447,425 B1
(45) Date of Patent: Sep. 10, 2002

(54) RANGE OF MOTION DEVICE

(75) Inventors: Harry Keller, Cambridge; Hans Fritschi, Mashpee; Ara Knaian, Cambridge, all of MA (US)

(73) Assignee: Paracomp, Inc., Cambridge, MA (US)

( * ) Notice: Subject to any disclaimer, the term of this patent is extended or adjusted under 35 U.S.C. 154(b) by 0 days.

(21) Appl. No.: 09/595,570

(22) Filed: Jun. 14, 2000

(51) Int. Cl.$^7$ ............................................... A63B 21/00
(52) U.S. Cl. ................................ 482/8; 601/33; 601/40
(58) Field of Search ........................ 485/1–9, 900–902; 601/1, 23, 27, 33–35, 40; 73/379.01, 379.02, 379.08

(56) References Cited

U.S. PATENT DOCUMENTS 4,538,595 A * 9/1985 Hajianpour ................ 601/33
4,875,469 A * 10/1989 Brook et al. ................ 601/40
5,620,410 A * 4/1997 Kasier et al. ............... 601/33

* cited by examiner

Primary Examiner—Glenn E. Richman (57) ABSTRACT

A flexure measurement device measures the flexure of a flexing body part thereby describing a range of motion of the body part. The flexure measurement device includes a flexible member and a sensor for detecting a change in proportion of the flexible member in response to flexing of the flexible member. In one example, a flexure measurement device measures a change in a length dimension of an elongated flexible member. The length dimension is measured using transmitted signals in which a light source directs a light beam across an array of light sensors. A change in length causes a light source to pivot, thereby changing the light sensors upon which the light beam impinges. The flexure measurement device determines a position in the array of light sensors at which the illumination changes from light to dark to produce a flexure angle measurement.

1 Claim, 9 Drawing Sheets

RANGE OF MOTION DEVICE

BACKGROUND OF THE INVENTION

Exercise has a primary importance in the course of recovery and rehabilitation from orthopedic surgeries, arthroscopies, skeletal traumas, and muscular injuries among patients in the general population. Exercise therapy is especially important among professional and amateur athletes. Efficient monitoring of therapy is highly desirable to deliver managed healthcare at high quality and reasonable costs, while ensuring the active participation of the patient.

Amateur athletes are found in high numbers among the population served by managed care organizations. Currently, an estimated 44 million people in the US participate in some form of exercise or sport. Every year approximately 35 percent of this population (15.4 million) experience a musculo-skeletal injury that is best treated using rehabilitative exercise, or surgical repair and physical therapy.

In addition, exercise is gaining acceptance as 'the fountain of youth" by our aging population. Many middle-aged people participate in various athletics. These people contribute to the population that is being treated for orthopedic injuries by managed care organizations.

Much medical and physiologic research shows a direct relationship between exercise and faster recovery in rehabilitation from orthopedic injuries, traumas, and surgeries. The period of time for recovery is often extended if exercise therapy does not proceed according to a prescribed duration, intensity, and frequency. Indeed, full recovery may not occur or the quality of the recovery is diminished if the exercise regimen is not pursued and fulfilled according to plan, or if exercise is not formally assigned by the caregiver.

A patient in the process of exercise therapy is directed to exercise at home, without supervision. Monitoring of the exercise therapy takes place at infrequent visits to a health care provider. Often monitoring indicates that the unsupervised exercise therapy is insufficient to achieve a quality recovery. The health care provider can detect that the unsupervised exercise therapy is insufficient but cannot determine how the therapy is lacking. The health care provider cannot determine whether the patient is failing to fulfill the prescribed exercise regiment or whether the patient is diligently performing the prescribed therapy but simply has a diminished capacity for exercise.

To date, no inexpensive technique is available for encouraging and monitoring a patient's pursuit of unsupervised physical and exercise therapy assignments following an injury, trauma, or surgery. Without the presence of a physical therapist, a trainer, or a $50,000.00 cybernetic, three-dimensional sensor/recorder/evaluation system, a patient's practice of an assigned physical or rehabilitation therapy is impossible to monitor. The patient is to be monitored to determine: (1) whether the patient is engaging in the exercise therapy as often as directed; (2) whether the patient is performing no more and no fewer repetitions than are assigned; and (3) whether the patient performs the exercises within a directed range of motion without significant discomfort. The range of motion typically increases over time as healing progresses with observable measures of improvement. The measures of improvement include decreased swelling, greater joint mobility, and increased muscular strength. However, the degree of improvement that permits a greater range of motion and function, the key issues in recovery, may be observed as infrequently as every seven to fourteen days over a period of several months. Unfortunately, the cost of more frequent visits to see a physician or physical therapist would be unacceptable for a managed care organization.

A further problem with unsupervised therapy and rehabilitation is the possibility of an adverse outcome. A normal scenario following the surgical repair of a trauma, a knee arthroscopy, an arthrotomy for a torn meniscus, or a surgery such as total hip arthroplasty, for example, is a healing with a predictable result of some degree of success. The normal scenario generally occurs when the treatment is biomechanically correct and appropriate, and all of the parameters of exercise are satisfied so that a normal recovery in light of the severity of the injury or the extent of the surgery. If the parameters of exercise or rehabilitation are not satisfied, an equally predictable outcome is a failure to recover within an acceptable "normal" standard.

A failure to recover muscular function and range of motion can become the subject of a lawsuit in which a patient claims that the surgical repair, arthroscopy, reconstruction, or the like was inadequately or incorrectly performed. A patient may bring suit against the institution treating the patient, the healthcare provider, and all persons involved in the patient's care. If no evidence of infection, neurologic damage, misalignment of bone ends or implant components, or other measurable and observable cause occurs to explain the functional failure, then inadequate rehabilitation may be deemed a cause of the patient's disability. For example, a patient may receive no physical therapy but rather is instructed to perform unsupervised rehabilitative exercises at home with periodic (generally weekly or biweekly) clinical visits to monitor the patient's progress. The patient may claim that the exercises did not help and that physical therapy was needed. A managed care organization or health care provider has little evidence supporting the premise that a prescribed exercise regimen is as effective as physical therapy. The managed care organization or health care provider has little evidence supporting the premise that the unsupervised exercise or therapy prescribed is appropriate but that the patient did not suitably follow directions and perform a suitable therapy regimen.

What is needed is a system and operating method for monitoring the unsupervised therapy of a patient that is simple, efficient, and cost-effective. What is further needed is a system and operating method that supplies information regarding the duration, intensity, and frequency of exercise therapy and rehabilitation.

SUMMARY OF THE INVENTION

A flexure measurement device measures the flexure of a flexing body part thereby describing a range of motion of the body part. The flexure measurement device includes a flexible member and a sensor for detecting a change in proportion of the flexible member in response to flexing of the flexible member. In one example, a flexure measurement device measures a change in a length dimension of an elongated flexible member. The length dimension is measured using transmitted signals in which a light source directs a light beam across an array of light sensors. A change in length causes a light source to pivot, thereby chanoing the light sensors upon which the light beam impinges. The flexure measurement device determines a position in the array of light sensors at which the illumination changes from light to dark to produce a flexure angle measurement.

In one embodiment of a flexure measurement device, a flexible member is connected to a plurality of small blocks. The individual blocks include an aperture for passing a line such as a fixed-length string and extending parallel to the flexible member. The blocks and apertures form a constant offset from the longitudinal body of the flexible member to the pathway of the string. The string is attached at a first end to a first end of the flexible member. When the flexible member is flexed, a second end of the string moves with respect to the flexible member. The displacement of the second end of the string is directly proportional to an angle formed by the first and second ends of the flexible member.

In accordance with another embodiment of the present invention, a flexure measurement device includes a sensor for measuring displacement including a plurality of light sensors and a light emitter. The light emitter is connected to a moveable assembly, such as a hinged assembly, in which a fixed portion of the moveable assembly, such as a hinge, is firmly connected to a flexible member having a first end and a second end. A fixed-length line has a first end affixed to the first end of the flexible member and a second end affixed to a moveable portion of the hinged assembly. The light emitter is also connected to the moveable portion of the hinged assembly and configured to produce a narrow beam. The fixed-length line moves with respect to the flexible member when the flexible member is flexed, causing the moveable portion of the hinged assembly and the light emitter to move, sweeping across the plurality of light sensors in the manner of a searchlight and activating particular light sensors when illuminated. The light sensors generate a digital output signal that is proportional to the movement of the hinged assembly and the motion of the flexible member. Gain of the digital output signal is adjusted by changing the point of attachment of a moving structure such as the fixed-length line with respect to the arm and by adjusting the distance from the light emitter to the plurality of light sensors.

In some embodiments, the light emitter is a light-emitting diode (LED) that is masked to generate a narrow illumination beam, and the plurality of light sensors is a charge-coupled device (CCD) array.

In some embodiments, a slide attachment is used rather than a pivot for attaching the light source. In some embodiments, the light source is held fixed while the light sensors are moved.

In another aspect of the present invention, a biomechanical monitoring system includes a flexure measurement device for monitoring a series of joint flexure measurements. The flexure measurement device transmits the joint flexure measurements via an interface to a database utilizing the Internet.

The described flexure measurement device, system, and operating method have many advantages. The flexure measurement device advantageously generates highly stable and repeatable measurements of the angle of a joint without aligning the device with the joint. The flexure measurement device advantageously is constructed in small, light, highly-portable forms for convenient usage in exercise applications and physical therapy applications. The flexure measurement device advantageously gives patients direct control over rehabilitation, avoiding soreness and injury that can accompany overly aggressive pursuit of exercise and ensuring compliance with a progression in range of motion, duration, intensity, and frequency when the process causes transitory discomfort.

BRIEF DESCRIPTION OF THE DRAWINGS

The features of the invention believed to be novel are specifically set forth in the appended claims. However, the invention itself, both as to its structure and method of operation, may best be understood by referring to the following description and accompanying drawings.

The use of the same reference symbols in different drawings indicates similar or identical items.

DESCRIPTION OF THE PREFERRED EMBODIMENT(S)

Figure 1:
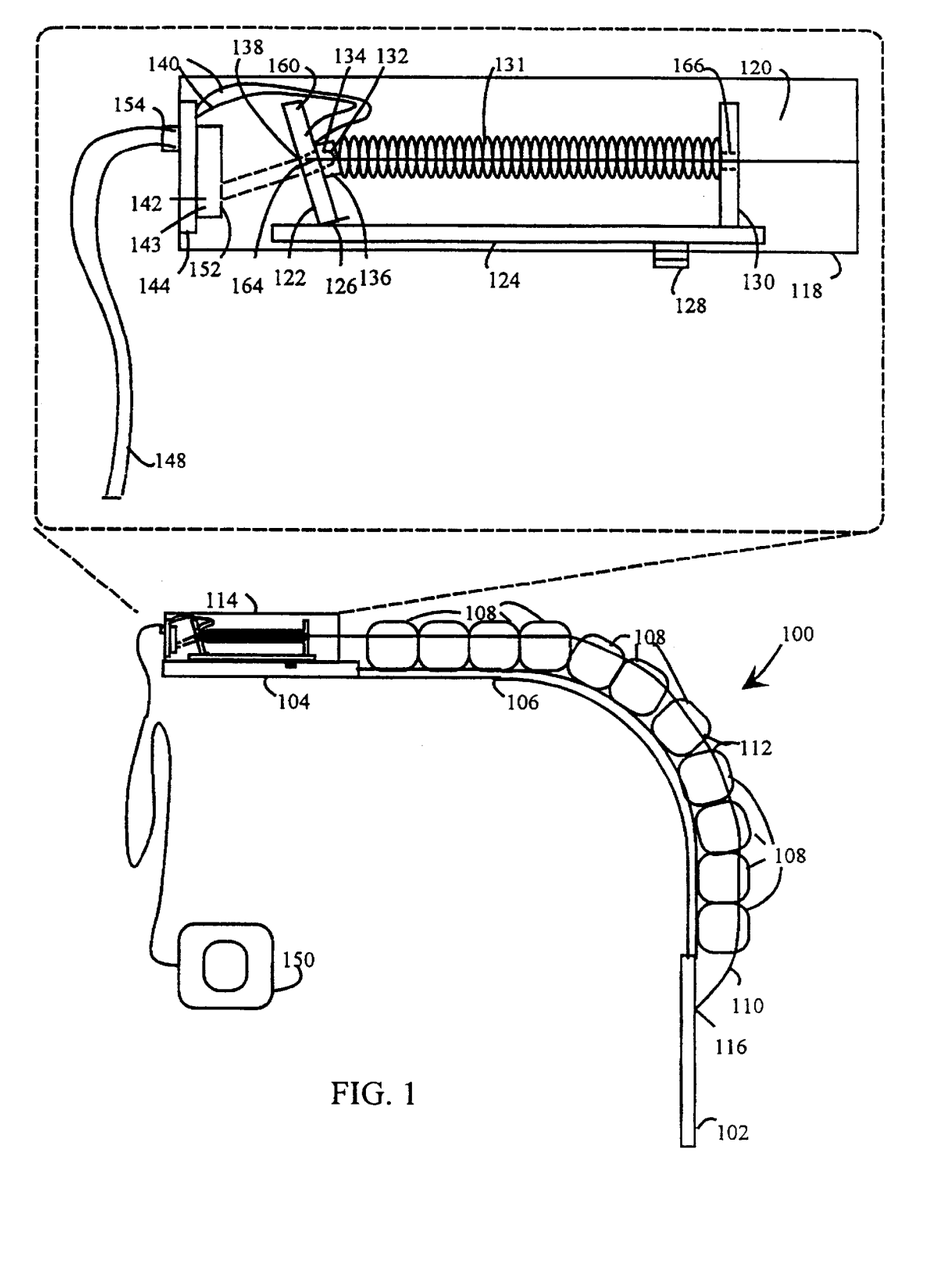
FIG. 1 is a schematic pictorial diagram illustrating an embodiment of a flexure measurement device.

Referring to FIG. 1, a schematic pictorial diagram illustrates an embodiment of a flexure measurement device 100. The flexure measurement device 100 is highly useful in applications including measurement of flexure of various portions of the human body or measurements of flexure of joints of exercise machines to measure, signal, and control changes in motion and range of motion. Biomechanical applications of the flexure measurement device 100 extend to and beyond any environment that employs range of motion exercise for rehabilitation, strength training, athletic training, sport-specific training, or analysis of human performance that involves linear joint motion.

The flexure measurement device 100 is particularly useful for applications including of flexure measurements along the linear axis of biomechanical joints in the extremities such as the wrist, the elbow, the shoulder, the ankle, the knee, and the hip. The device may also be used for other joints. The flexure measurement device 100 is also useful in other applications including measurements in which the range of motion is determined for symmetrical or nonsymmetrical joints and in applications for which an object bends about a single joint or a plurality of joints so that a flexure measurement is made in one or more planes to continuously monitor and control flexure of the joint or joints.

The flexure measurement device 100 measures hinge-type joint movement, or flexion and extension in one plane. The flexure measurement device 100 is highly suitable for measuring joint motion and monitoring exercise in the human knee, since the knee primarily flexes and extends in one plane. The restricted motion of the knee combined with its critical role in high speed locomotion makes the knee, the joint that is most often injured during sustained athletic endeavor.

The flexure measurement device 100 measures the motion of any joint in one plane and generates data resulting from the measurement. Joints such as the hip, ankle, shoulder, elbow, and wrist are capable of several types of movement in more than one plane. The flexure measurement device 100 is useful for measuring, monitoring, and testing the movement in two directions, for example forward and back, or side to side, when the movement is executed in one direction at a time in the manner of a hinge.

The flexure measurement device 100 is useful not only for biomechanical applications but also for mechanical applications. The flexure measurement device 100 is generally useful for supplying a method of measuring and controlling flexure of any object that bends or rotates about a joint or hinge such that the measurement and control is accurate and precise and not subject to deterioration due to wear and breakage.

The flexure measurement device 100 includes a first mount 102 and a second mount 104 that are connected by an elongated flexible coupling member 106. The first mount 102 and the second mount 104 are rigid structures constructed from any suitable material, most typically a plastic material. The first mount 102 and the second mount 104 are formed in any suitable size and shape, most typically a size chosen based on the body part to which the flexure measurement device 100 is to be attached and most typically a flat shape with rounded edges. The construction material and shape of the first mount 102 and the second mount 104 are selected based on the particular intended biomechanical purpose of the flexure measurement device 100. The first mount 102 and the second mount 104 are connected to a body part or limb by one of many suitable attachment devices such as nylon straps, elastic bands, Velcro™ straps, Neoprene sleeves, mesh bandages, and the like.

The elongated flexible coupling member 106 is constructed from any suitable flexible material, for example a flexible plastic or nylon. Dimensions of the flexible coupling member 106 are selected based on the biomechanical application of the flexure measurement device 100 and the body part to which the flexure measurement device 100 is applied. In the illustrative example, a plurality of carriers 108 are mounted to the flexible coupling member 106 using any suitable adhesive or attachment structures, for example screws. The carriers 108 are suitable structures for channeling a line 110 a desired distance from the flexible coupling member 106. In the illustrative example, the carriers 108 are blocks that are perforated with holes 112 in which the line 110 is threaded. The carriers 108 are constructed from a suitable material such as a plastic, Teflon, or the like and have any suitable shape and size. Exemplary shapes include blocks, spheres, or any other suitable geometric shapes. The size and shape of the carriers 108 are selected based on the biomechanical application of the flexure measurement device 100 and the body part to which the flexure measurement device 100 is applied. In one example, the holes 112 in the carriers 108 separate the line 110 from the flexible coupling member 106 by a 1–25 millimeters although larger and smaller distances are warranted for some applications. The line 110 is generally a non-elastic, durable string or tape.

In other embodiments, the flexible coupling member 106 may take various other forms. Typically, the flexible member is semi-articulated so that the range of motion and the length change during flexure are superior to flexing characteristics of a solid, flexible material.

In some configurations, a flexible member is semi-articulated by formation of notches alternately on opposite sides of the member so that a central longitudinal line of the member has an invariant length.

In other configurations, a flexible member has notches formed on only one side so that a side of the member opposite the notched side has an invariant length. Ends of a flexible coupling member remain perpendicular to the line of curvature resulting in a precise measurement of the radius of curvature.

The line 110 is affixed at a first end 116 to the first mount 102, constrained by the carries 108, and affixed at a second end 118 to a sensor assembly 114 that is mounted on the second mount 104. In the illustrative example, the line 110 is constrained by the carriers 108 by threading the line 110 through the holes 112 in the carriers 108. The line 110 is constructed from a sufficiently durable material to withstand longitudinal and transverse stresses. For example, the line 110 is formed from a heavy-duty fish line or monofilament line.

The line 110 is used to sense changes in relative angle between the first mount 102 and the second mount 104. When the flexure measurement device 100 is flexed, the flexible coupling member 106 bends but maintains a constant length. In contrast, as the flexure measurement device 100 is flexed, the line 110 changes length and the change in length is propagated to the sensor assembly 114.

The sensor assembly 114 includes an essentially light-tight housing 118 having an aperture 116 for passing the line 110. The line 110 passes through a chamber 120 within the housing and is affixed to a hinged member 122 that is attached to an adjustable bar 124 by a hinge 126. In the illustrative flexure measurement device 100, the hinged member 122 is a rectangular plastic piece although the member may otherwise have various other suitable shapes, sizes, and compositions. Longitudinal placement of the adjustable bar 124 within the housing 118 is adjusted by disengaging or loosening an adjustment fastener such as a threaded bolt 128, sliding the adjustable bar 124 with reference to the housing 118, and engaging or tightening the fastener. The position of the adjustable bar 124 is adjusted to regulate the sensitivity of the flexure measurement. The hinged member 122 moves as the flexible coupling member 106 is flexed but is kept under tension by a tension device 131 such as a spring. In the illustrative example, the spring is held between the hinged member 122 and a support 130 that is firmly attached to the adjustable bar 124.

The light housing 136 is mounted on a lateral wall of the housing 118 and includes a rectangular piece of plastic 160 that is mounted to the hinge 126. The hinge 126 is positioned at the end of the plastic piece 160 nearest to the emission detector 142. The support 130 protrudes perpendicular to the rectangular piece of plastic 160 and restrains the rectangular piece of plastic 160 from bending farther than a 90° angle. Both the rectangular piece of plastic 160 and the support 130 include generally centrally-located aperture 164 and 166, respectively, that are a suitable size for threading the line 110. A light-emitting diode (LED) 134 is fitted through the aperture 164, in the rectangular piece of plastic 160 and the tension device 131 is positioned between the rectangular piece of plastic 160 and the support 130. One end of the line 110 is firmly attached to the rectangular piece of plastic 160 and extends through the apertures 164 and 166, through a vacant interior cavity of the tension device 131, and channeled through the carriers 108 to a point of attachment on the first mount 102.

An emission device 132 is attached to the hinged member 122 and generates an emission signal indicative of movement of the hinged member 122. In the exemplary embodiment, the emission device 132 includes a light-emitting diode (LED) 134 enclosed within a light housing 136. In the example, the light housing 136 has the form of a cylinder. The light housing 136 is light-tight except for an illumination window or slit 138 that is oriented at a suitable angle for producing a sensitive indication of movement of the hinged member 122. For example, the slit 138 is aligned to have a longest dimension that is parallel to the axis of rotation of the hinged member 122. Two wires 140 are attached to the light housing 136 for powering the LED 134.

Light emitted from the emission device 132, is detected by an emission detector 142. In the exemplary flexure measurement device 100, the emission detector 142 is a charge-coupled device (CCD) array 143 that is mounted on a circuit board 144 affixed to an end wall of the housing 118. The emission device 132 emits a bar of light that is detected by the emission detector 142. Detecting elements of the CCD array 143 of the emission detector 142 are arranged in a narrow strip that is aligned perpendicular to the bar of light produced by the emission device 132 so that the CCD array elements detect only the intersection of the bar of light and the array element strip. The arrangement is such that if tension is imposed on the line 110, the LED 134 is pulled to a different orientation with respect to the CCD array 143 so that movement of the hinged member 122 around the hinge 126 causes light from the LED 134 to sweep across the array of charge-coupled devices (CCDs) 143. By determining which element of the CCD array 143 is the last or first in sequence to sense the light, the position of the LED 134 and therefore the position of the hinged member 122 is detected. The position of the hinged member 122 is further indicative of the change in length difference of the line 110 with respect to the pathway through the carriers 108 and indicative of the angle of flexure. The position of the bar of light impinging on the emission detector 142 is detected and transmitted via a signal cable 148 that is connectable to a receptor 154 mounted on the end wall of the housing 118 adjacent the circuit board 144. The receptor 154 is electrically connected to array elements of the CCD array 143. The CCD array 143 is a digital sensor that advantageously eliminates problems of drift and calibration associated with analog flexure measurements.

In an illustrative example, the emission device 132 produces a red-orange light and the emission detector 142 is covered with a blue filter 152 to reduce the amount of light illuminating the CCD array 143 so that only the CCD array elements at the point of intersection produce a signal. In other embodiments, other known techniques may be used to suitably encode the signal produced by the emission device 132 and the emission detector 142. Typically the emission detector 142 is highly light-sensitive. Accordingly, the light housing 136 and the housing 118 are shaded a flat black color to absorb extraneous light and the housing 118 is well-sealed.

The flexure measurement device 100 detects flexure by detecting differences in length between the line 110 and the flexible coupling member 106. As the flexure measurement device 100 flexes, the curve formed by the line 110 and the curve formed by the flexible coupling member 106 vary relatively in length. In particular, the length of the flexible coupling member 106 remains constant while the length of the line 110 varies. The relative length of the line 110 in comparison to the flexible coupling member 106 length varies in direct proportion to the relative angle between the first mount 102 and the second mount 104. Thus, the flexure measurement device 100 measures flexure simply by detecting the variation in angle at the ends of the device.

The signal cable 148 is connectable to a power and display unit 150. The signal cable 148 has a length selected from various suitable lengths according to the biomechanical application of the flexure measurement device 100 and the body part to which the flexure measurement device 100 is applied.

Operation of the flexure measurement device 100 is described by considering a particular device embodiment. The flexure measurement device 100 is mounted laterally on a selected joint and properly positioned to measure and record the linear range of motion of the joint. An illustrative flexure measurement device includes an elongated flexible articulated member which forms a pathway for passage of a flexible, non-elastic line having a length that remains constant while the pathway of the line changes in length during flexure. The difference in length between the line and the pathway is sensed by a digital device utilizing light and a light sensor array to determine the angle of flexure. The flexure measurement device is attached to a flexing structure, either mechanical or biomechanical, so that, when the flexing structure flexes, the flexure measurement device also flexes. As the flexure measurement device flexes, the length of the pathway either increases or decreases with respect to a constant-length line of curvature of the flexible articulated member. During flexure of the articulate member, ends of the articulated member remain approximately perpendicular to the constant-length line of curvature of the articulated member. As a result, the difference in length along different longitudinal portions of the articulated member are proportional to the thickness of the articulated member times the angle of curvature (assuming a circular curvature). The flexure measurement device 100 is monitored to determine the number of times (sets) the exercise is performed, the number of repetitions carried out in a set, and the actual arc of motion, recorded in degrees, for every repetition, with an accuracy of one or two degrees.

Figure 2:
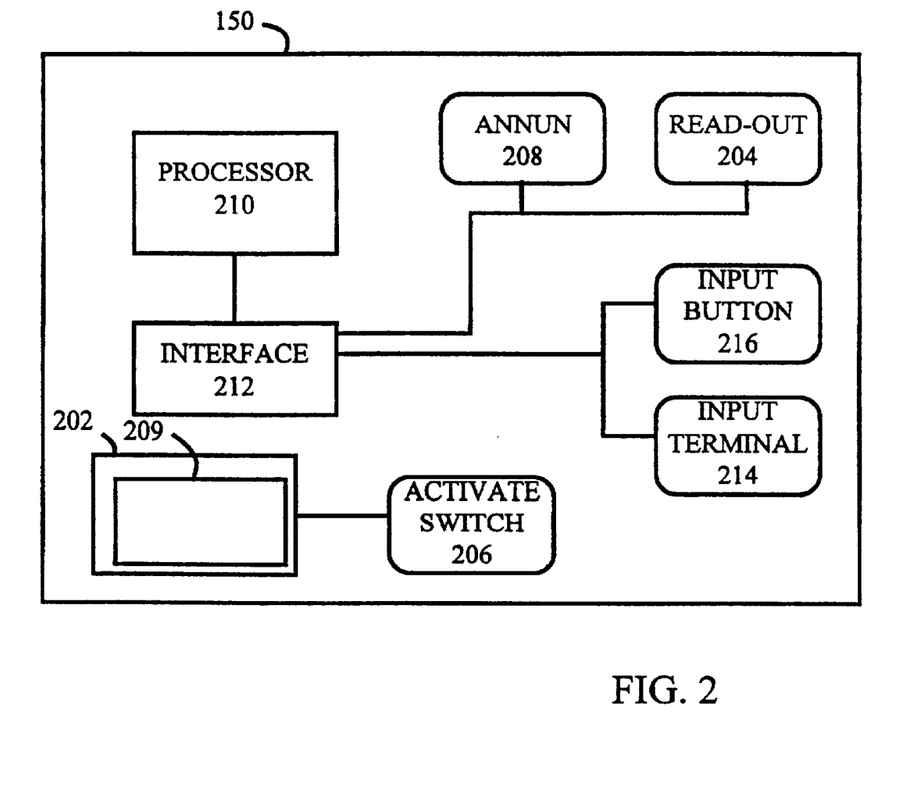
FIG. 2 is a schematic block diagram that shows a suitable display for usage with the flexure measurement device.

Referring to FIG. 2 in conjunction with FIG. 1, a schematic block diagram illustrates an embodiment of a suitable power and display unit 150 for usage with the flexure measurement device 100. A simple version of the power and display unit 150 includes a processor 210, a battery mount 202, an input terminal 214 for connection to the signal cable 148, a read-out device 204, an annunciator 208, an input button 216, and an activation switch 206. The read-out device 204, the annunciator 208, the input button 216, and the input terminal 214 are connected to the processor 210 via a interface 212 such as a conventional parallel interface, serial interface, or any other suitable interface. In the illustrative power and display unit 150, the battery mount 202 is configured to accept a 9 V battery. The activation switch 206 is connected between the battery mount 202 and circuitry including the processor 210, the read-out device 204, and the annunciator 208 control activation and deactivation of the power and display unit 150. One example of a suitable read-out device 204 is a liquid-crystal diode (LCD) visual display unit.

During operation, batteries 209 are installed in the battery mount 202 and the signal cable 148 is attached to a cable connector 210. The power and display unit 150 is activated by actuating the activation switch 206 in an "ON" position. The read-out device 204 is observed to monitor variations in angle of the first mount 102 and the second mount 104 of the flexure measurement device 100. When the angle does not change, the value displayed on the read-out device 204 is stable. The read-out value is well-correlated to the angle. The flexure measurement device 100 is generally insensitive to variations in position of the first mount 102 and the second mount 104 but highly sensitive to the relative angle of the ends of the flexure measurement device 100.

The flexure measurement device 100 is attached to a body part or limb using an attachment device such as Velcro™ straps and positioning the first mount 102 and the second mount 104 in a suitable configuration. One exemplary implementation is a flexure measurement device 100 that is configured in an appropriate shape and size for measuring flexure of the knee. The first mount 102 is positioned on the lower leg and the second mount 104 with the attached housing 118 is positioned on the upper leg. The flexible coupling member 106 flexes to accommodate movement of the lower leg at the knee. The flexure measurement device 100 is further positioned so that the housing 118 is located on the outer portion of the upper leg when the lower leg is extended with essentially no bend in the knee.

As the knee flexes, the flexible coupling member 106 bends so that tension is placed on the line 110, pulling the hinged member 122 and the LED 134 in the light housing 136 at the hinge 126, illuminating a larger portion of the CCD array 143. The CCD array 143 generates a signal indicative of the number of illuminated elements in the CCD array 143. The signal is transmitted to the power and display unit 150 via the signal cable 148 and passed to the processor 210 via the input terminal 214. The processor 210 receives the illumination signal, calculates an angle of flexure based on the illumination signal, formats the calculated angle of flexure, and displays the formatted angle of flexure on the read-out device 204.

The processor 210 executes various programs and routines for controlling the flexure measurement device 100 or accessing information generated by the flexure measurement device 100.

One exemplary routine is useful for defining a range of motion of flexure. When the input button 216 is actuated or depressed, the processor 210 is interrupted. The processor 210 executes an interrupt service routine that accesses the current reading of the illumination signal from the flexure measurement device 100 and stores the signal reading in a memory. A desired angle is defined by depressing the input button 216 when the flexure measurement device 100 is flexed to a selected angle. Thereafter, the range of motion service routine monitors the signal from the flexure measurement device 100 and generates an angle signal whenever the flexure angle passes the selected angle. The annunciator 208 may be enabled to emit a tone at the occurrence of each angle signal. In this manner, the flexure measurement device 100 is used to define a range of motion. Although the annunciator 208 is described as a device for generating an audio signal, in other examples an annunciator may generate visual, tactile, or other signals to indicate a predetermined flexure value.

The power and display unit 150 is programmed the input button 216 to produce tones at the limits of a predetermined range of flexions and extensions. The limits of the range are typically set and advanced as healing takes place. The annunciator 208 generates tones that inform a patient or exerciser that the flexure is in a proper range and, if desired, motivates the patient or exerciser through periods of mild discomfort. The power and display unit 150 may also be programmed to identify instances when a patient or exerciser extends or flexes a limb beyond the preset range. In one example, two additional, higher-pitched tones are automatically set at ten degrees beyond the selected limits for flexion and extension. Consistent sounding of the two higher-pitched tones is a signal that the preset range of motion is to be increased.

The range of motion service routine may be used to set both a low angle of flexure and a high angle of flexure and to emit a tone, for example at different frequencies, when the angle transitions below a low angle limit and exceeds a high angle limit.

In exercise applications, information concerning the range of motion is useful to an athlete or trainer for directing an exercise program. In rehabilitation therapy applications, the range of motion information is highly useful to a patient or therapist for determining a safe and therapeutic motion. In various embodiments, the flexure measurement device 100 supplies signals indicative of the measurement of range of motion and, through visual, audible, tactile, and/or other means, supplies feedback to a user to control the range of motion.

The tones emitted at the preset limits of flexion and extension during movement identify the prescribed terminal points of the exercise and may be motivational factor for patients in unsupervised exercise. Consistent sounding of a second tone a few (for example 10°) degrees beyond the sounding of a first tone during supervised exercise may be a reliable indicator for increasing the range of motion of the exercise during a patient's progression to normal function. All tones are markers that are recorded during every exercise movement. If a patient exceeds the prescribed range of motion regularly or fail to achieve the range, that information is included in the data report.

Advantageously, the flexure measurement device 100 immediately informs a patient of success and improvement every time the patient exercises, an encouragement that is lacking from conventional home exercise equipment.

In industrial applications, the flexure measurement device 100 is highly useful for continuously measuring flexure of a machine or portion of the machine in which the measurement is complicated by usage of a non-symmetrical joint.

The flexure measurement device 100 and power and display unit 150, in combination, form a flexure measurement and control device that is simple in construction and easy to use.

Figure 3:
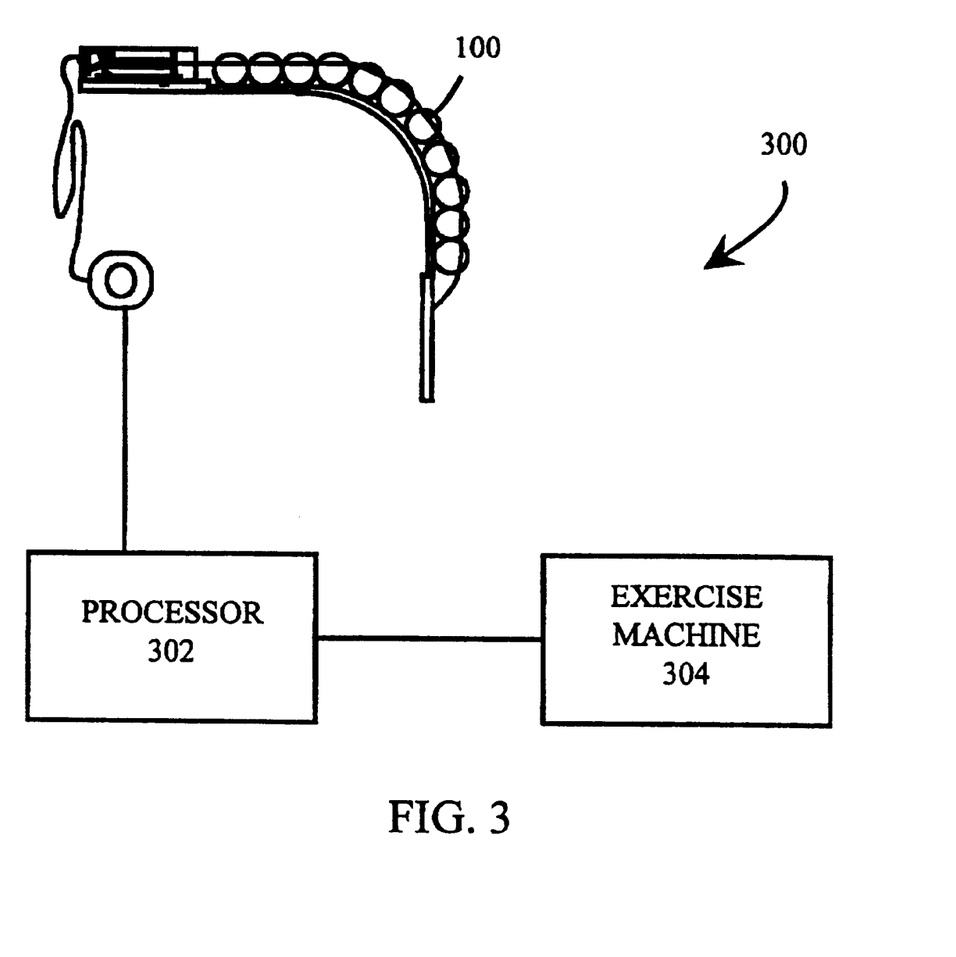
FIG. 3 is a schematic block diagram illustrating an exercise or rehabilitation therapy system utilizing the flexure measurement device.

Referring to FIG. 3, a schematic block diagram illustrates an exercise or rehabilitation therapy system 300 utilizing the flexure measurement device 100. The flexure measurement device 100 is communicatively connected to a processor 302 connected to an exercise machine 304. The processor 302 receives reliable and accurate flexure measurement from the flexure measurement device 100 and also receives feedback signals from the exercise machine 304 to allow the processor 302 to program the exercise machine 304 for maximum benefit of the user.

A joint that is stiff and swollen after a recent injury, arthroscopy, or open surgery generally has a limited range of motion. The exercise or rehabilitation therapy system 300 supplies to a caregiver two features that address the limited motion range condition. First, the exercise or rehabilitation therapy system 300 sets a specific range of motion with limits on flexion and extension to simultaneously control, evaluate, and encourage rehabilitation exercise. Second, the exercise or rehabilitation therapy system 300 sounds a tone when the limits are exceeded by a predetermined amount, for example one or two degrees, and a second, higher-pitched tone is sounded when the limits are exceeded by a more significant amount, for example more than 10 degrees.

An operation of setting limits for the arc of motion tracked by the exercise or rehabilitation therapy system 300 is highly advantageous to allow a caregiver to identify a patient's range of motion and capacity for exercise when rehabilitation begins. The range is then gradually expanded as the patient condition progresses during the healing process. The exercise or rehabilitation therapy system 300 is also used for testing specific segments of the range of motion, and for creating exacting programs that help prevent further injury by improving the balance of agonist and antagonist muscle activation.

The exercise or rehabilitation therapy system 300 supports the psychological component of motivation in the therapeutic process of exercise by sounding a tone at the prescribed limits of flexion and extension. Transitory discomfort causes some patients to decrease effort in fearful anticipation of increasing pain. The exercise or rehabilitation therapy system 300 establishes a "safety zone" of exercise that helps eliminate the fear. During exercise, the sounding of the tone represents successful effort and encourages the patient to flex or extend a stiff, post-surgical, or post-traumatic joint, until the patient hears the tone at both terminal points in the movement. The tone becomes both a motivational aid and a signal of accomplishment when the exercise is moderately painful or challenging. At the same time, the exercise or rehabilitation therapy system 300 advantageously supplies to caregivers, managed care organizations, and insurance companies a record showing whether a patient successfully meets therapeutic goals. A patient may exercise with greater regularity and recover faster, because the patient receives an immediate indication of success or an indication to exert harder for every movement, during each exercise session.

Figure 4:
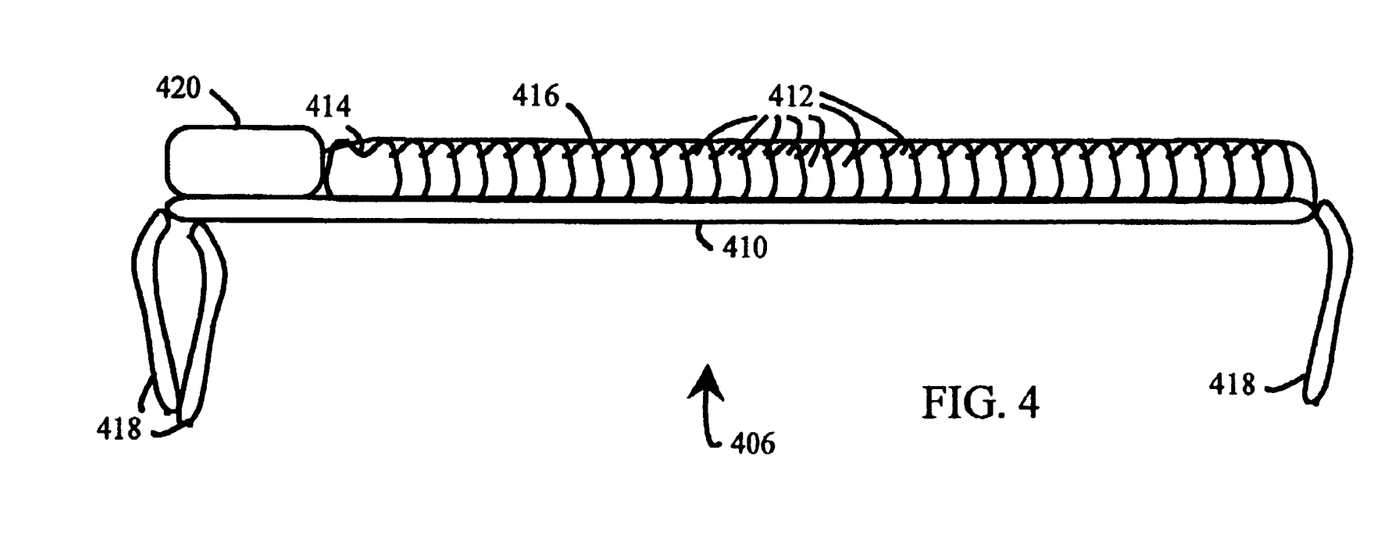
FIG. 4 is a schematic pictorial diagram illustrating an alternative embodiment of a flexible coupling member.

Referring to FIG. 4, a schematic pictorial diagram illustrates an alternative embodiment of a flexible coupling member 406. The flexible coupling member 406 is formed by a nylon member 410 of rectangular cross-section having pieces of nylon 412 attached on one side to create the effect of a single-side notched flexible member. A groove 414 is made through the outside of the pieces of nylon to allow a length of a monofilament line 416, to pass unhindered within the groove 414. A plurality of pieces of polycarbonate 418 are attached to first and second ends of the nylon member to facilitate secure attachment to the leg or arm of a person. The monofilament line 416 is securely attached to a first end of the nylon member 406. A small box 420 containing a sensor (not shown) is attached to a second end of the nylon member 406. The monofilament line 416 enters the box from one end and connected to the sensor.

Figure 5:
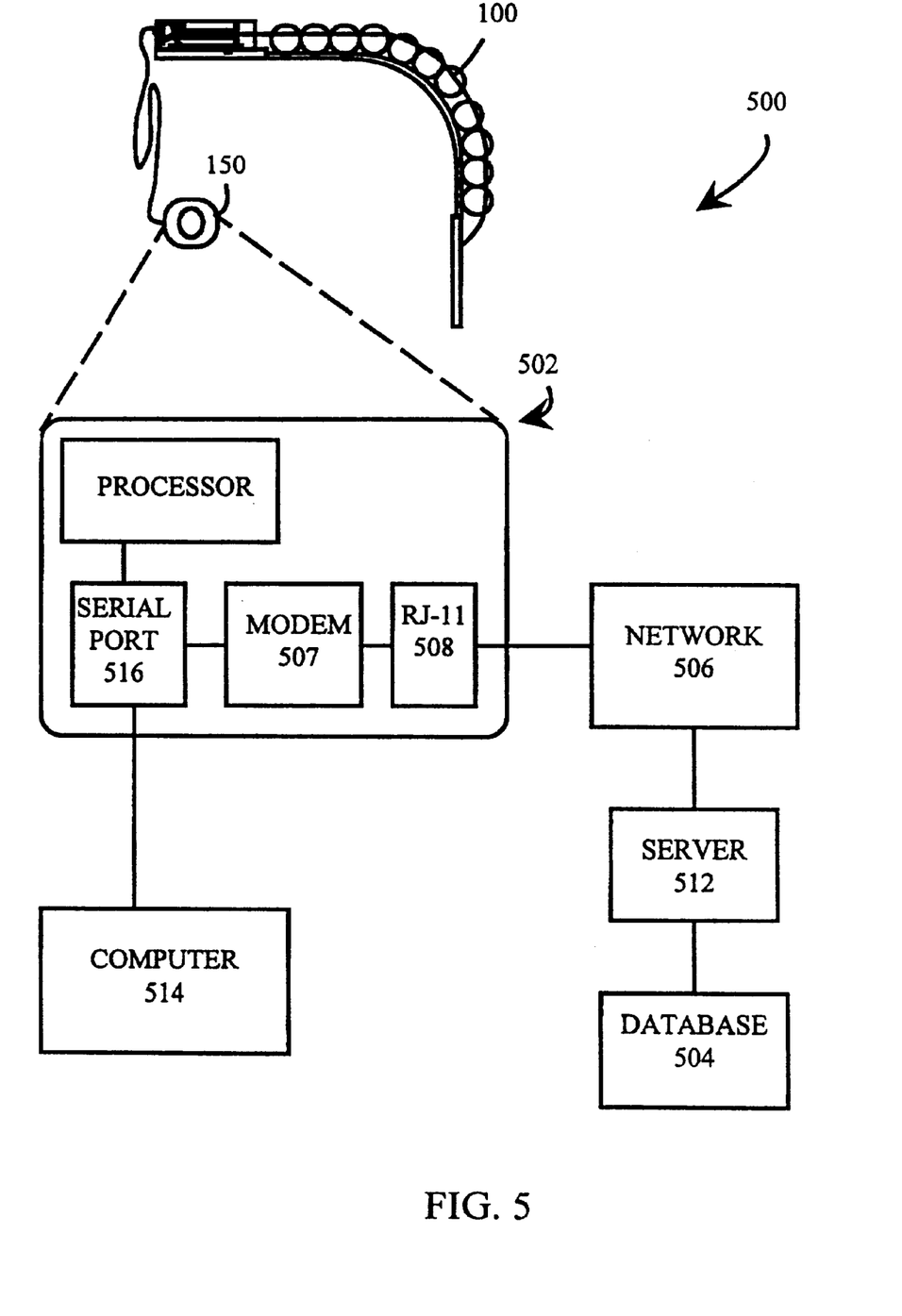
FIG. 5 is a shematic pictorial drawing illustrating a complete system for acquiring, storing, and using data from the flexure measuring device.

Referring to FIG. 5, a schematic block diagram illustrates a biomechanical monitoring system 500 that includes the flexure measurement device 100 for monitoring a series of joint flexure measurements. In an illustrative embodiment, the biomechanical monitoring system 500 is a fully portable, battery-powered sensor and controller/recorder that can be used at home. The biomechanical monitoring system 500 provides accurate measurement, monitoring, recording, and communication of range of motion during post-surgical or post-traumatic exercise of the extremities across an arc of more than 100 degrees.

The flexure measurement device 100 transmits the joint flexure measurements via an interface 502 to a computer 514 or to a database 504 utilizing a network 506 such as the Internet. One suitable interface 502 includes the power and display unit 150 connected to a personal computer 514 via a serial port 516. The computer 514 executes software particularly adapted for communicating with the power and display unit 150, receiving data generated by the flexure measurement device 100, and supplying control parameters for controlling operations of the power and display unit 150 and the flexure measurement device 100.

The interface 502 includes the power and display unit 150 with a modem 507 connected to an RJ-11 telephone jack 508 for connecting to regular telephone lines 510. In one operation, the power and display unit 150 makes a telephone access of a toll-free number to establish a communication session with a network server 512. Flexure data acquired by the flexure measurement device 100 is uploaded to the network server 512. Uploaded data is typically processed and transmitted to a Web site of a health care provider such as, but not limited to, managed care hospitals, orthopedic and sports medicine practices, rehabilitation centers, physical therapists, professional sports conditioning coaches, athletic trainers, a centralized location determined by a managed care system for storage of multiple data receivers, and the like (not shown), often in a fee-based relationship.

A typical interaction with a health care provider or trainer may include downloading and analysis of data on a daily or weekly basis, for example, using an exercise protocol that is specified in advance by physicians and physical therapists using dedicated software. The network server 512 suitably resets and recalibrates the flexure measurement device 100 by sending commands via the interface 502.

The power and display unit 150 typically downloads accumulated information accumulated to a centralized storage such as a computer (PC) located at any managed care hospital, or at its orthopedic, sports medicine, and physical therapy clinics, or at a server dedicated to this purpose, and accessible by multiple users. A similar station can be created at athletic training and professional sports conditioning and rehabilitation facilities, or downloading can be accomplished at the Web site.

A new exercise regimen may be quickly uploaded from a PC to the exercise or rehabilitation therapy system in a preemptive initiation of the next phase in a preplanned recovery program that is triggered by input received from the patient's recorder. In some embodiments, wireless transmission of the upload data is possible, for example by holding the device against a telephone for data transmission to and from the dedicated PC.

An automated, interactive, upload and download sequence via the Internet connection, of at the PC, may respond to receipt of data classified as a normal condition by maintaining operational parameters at the same levels or by advancing the operating parameters to a gentle increase in range of motion. A typical response to receipt of data classified as abnormal is a flagging of reports that indicate rehabilitative intervention by a physician or physical therapist when the data does not at least minimally fulfill the parameters of the exercise protocol.

In some embodiments, Java™ technology is implemented in the flexure measurement device 100, the power and display unit 150, and the network server 512, interacting with the computer of the health care provider via Java™ applets.

Advantageously, the biomechanical monitoring system 500 accurately monitors rehabilitative exercise, encourages patient progress, simplifies documentation, assists maintenance of high standards of patient care, and results in additional control over therapy to key caregivers.

The exercise or rehabilitation therapy system creates a record for managed care organizations that cannot afford to provide physical therapy or regularly track the rehabilitation of a patient recovering from orthopedic surgery. The exercise or rehabilitation therapy system helps focus the resources of the organization on those patients needing the most care.

Figure 6:
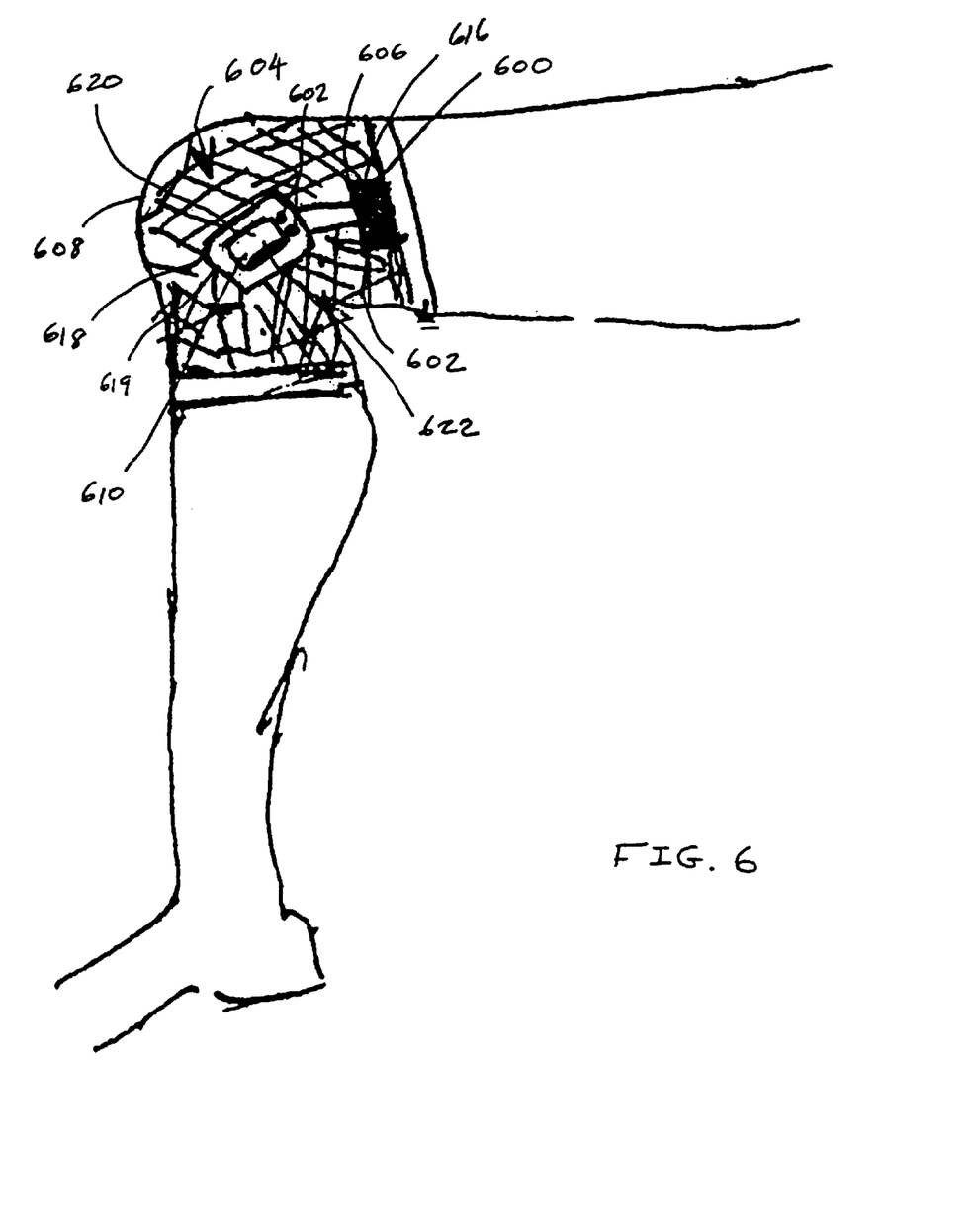
FIG. 6 is a pictorial diagram illustrating an embodiment of a flexure measurement device that is positioned on a patient's knee using a sheath.

Referring to FIG. 6, a pictorial diagram illustrates an embodiment of a flexure measurement device 600 that is positioned on a patient's knee by a sheath 602 that is sewn to the lateral side of a mesh or neoprene cuff 604 with hook and loop closures 606 that fit around the knee. The sheath 602 holds the flexure measurement device 600 in place alongside the knee. A patellar cutout 608 ensures proper orientation and positioning on any size leg. In some embodiments, the sheath 602 includes a pouch 618 with a Velcro™ closure 619 for holding a power and display unit 620 having a cut-out 622 so that a readout 610 such as an LCD readout of the device in degrees, is visible. The illustrative flexure measurement device 600. Operation is controlled by two buttons 612.

Embodiments utilizing a mesh include a piece of bandaging mesh 604, similar or the same as a mesh for holding a bandage in place over a scrape across a joint such as the knee or elbow. In athletes with a scrape injury, such as bicyclists, movement is desirable during the healing process so that the scar tissue does not limit range of motion and so that the traumatized muscle suffering from the impact (mild crushing) injury is not permitted to develop flexion contracture due to spasm, contusion, and pain upon motion. Exercising of the limb as quickly as possible avoids these difficulties. In this manner, the mesh allows nearly immediate exercise to avoid atrophy of the valuable muscle mass.

The mesh bandage is useful in an athletic environment in preference to a tape bandage because sweat and movement conspire to pull tape away that holds a bandage in place. Furthermore, taping may restrict the range of motion of the limb. Tugging on the tape caused by motion of the limb may irritate the healing wound, resulting in pain that also limits the range of motion.

In contrast, mesh is effective for holding a dressing in place since the position is maintained by a ubiquitous system of interlocking threads that will flex during normal range of motion, but do not limit motion or cause painful pressure on the wound. The tube of mesh is normally tied in place at a top and bottom extremity or taped along an edge removed from the wound.

The entire sheath 602 structure is nonrigid except for rubberized, non-slip, elastic bands 614 at the top and bottom edges of the mesh "tube" that will hold the mesh 604 in position during range of motion studies, and a pocket 616 along a lateral aspect of the mesh 604 into which the flexure measurement device 100 is placed.

Figure 7:
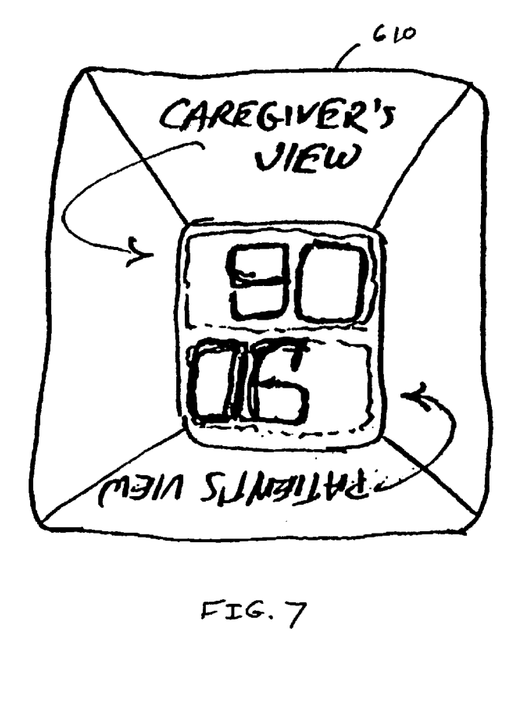
FIG. 7 is a schematic pictorial diagram illustrating a suitable readout.

The illustrative flexure measurement device 600 mounts in a lateral sheath 602, and the power and display unit 620 includes electronics, a power supply, and readout 610 positioned on the proximal thigh. The readout 610 is readable from two positions, 180 degrees removed, so that both a caregiver and patient can see the readout 610 simultaneously as is illustrated in FIG. 7, a schematic pictorial diagram illustrating a suitable readout 610.

Figure 8:
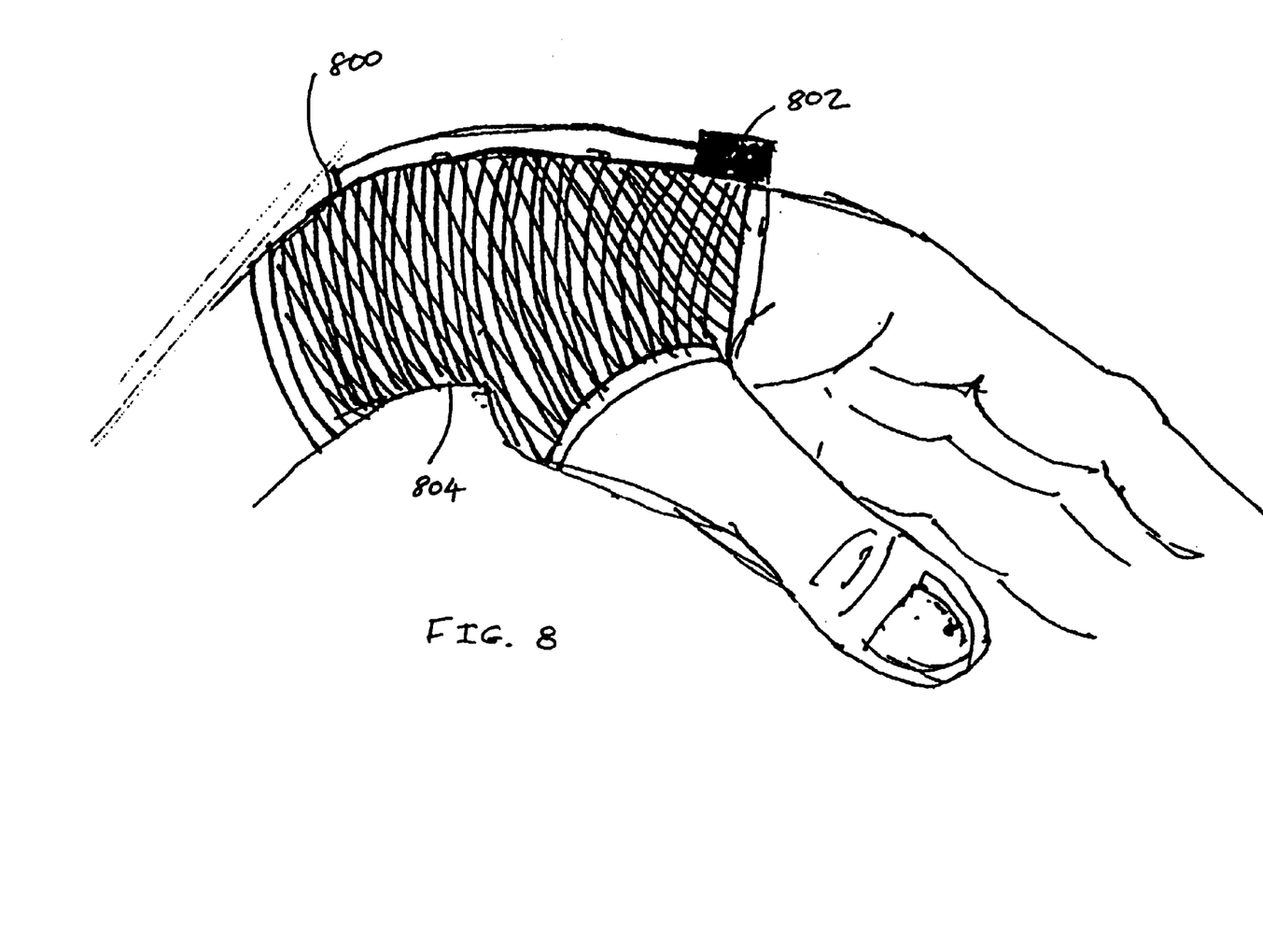
FIG. 8 is a schematic pictorial diagram illustrating an embodiment of a wrist attachment mounting for a flexure measurement device.

Referring to FIG. 8, a schematic pictorial diagram illustrates an embodiment of a wrist attachment mounting 800 for a flexure measurement device 802. The wrist attachment mounting 800 includes a mesh tube 804 with finger and thumb cut-outs. The flexure measurement device 802 is attached along the back of the hand so that flexion and extension are measured.

Figure 9:
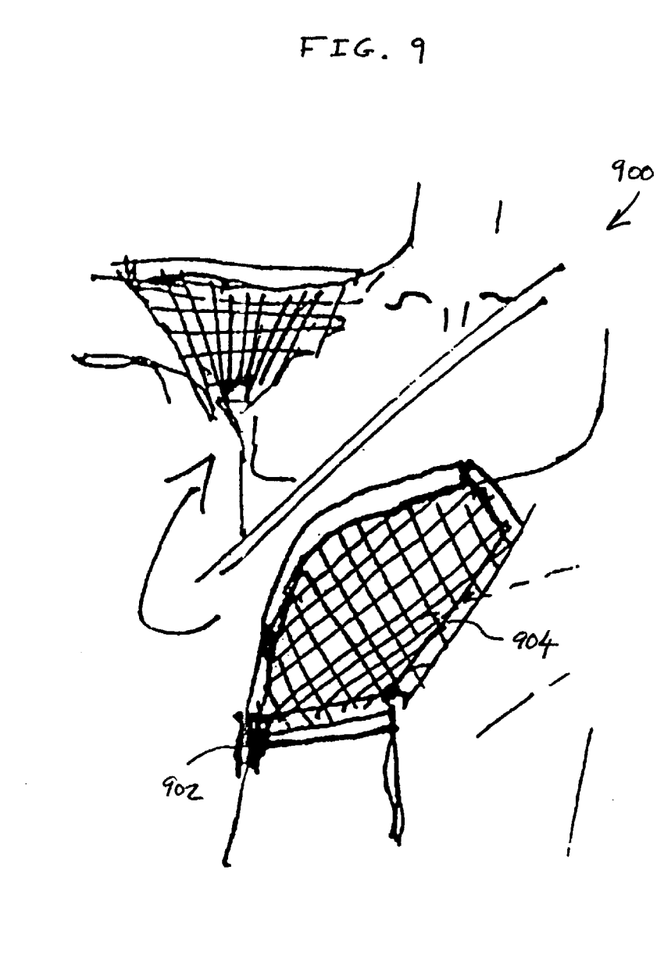
FIG. 9 is a schematic pictorial diagram showing an embodiment of a shoulder attachment mounting for a flexure measurement device.

Referring to FIG. 9, a schematic pictorial diagram illustrates an embodiment of a shoulder attachment mounting 900 for a flexure measurement device 902. The shoulder attachment mounting 900 includes a mesh tube 904 that is positioned by sliding the tube up the arm. The flexure measurement device 902 is positioned on the top of the shoulder so that lateral shoulder flexion is measured.

Figure 10:
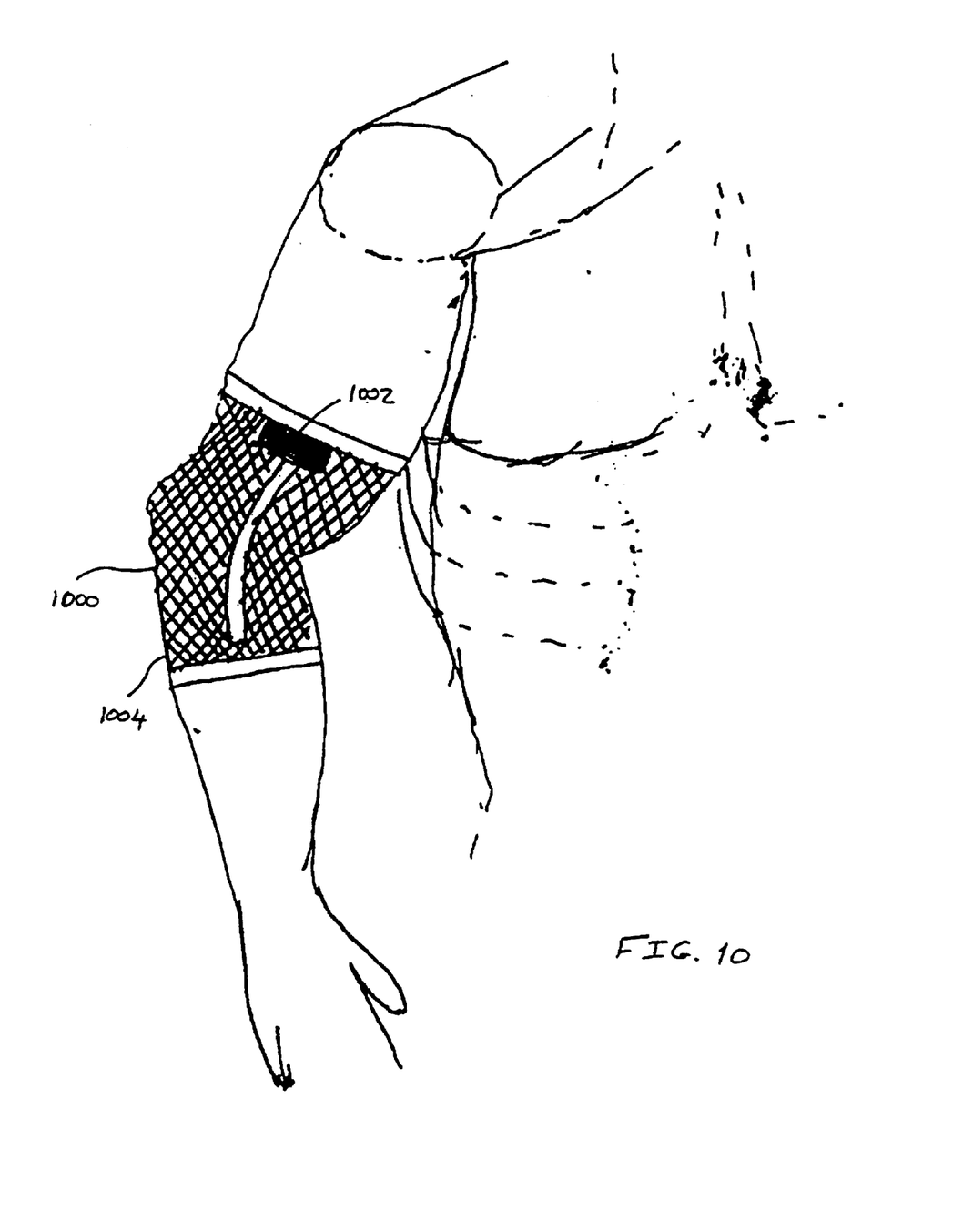
FIG. 10 is a schematic pictorial diagram illustrating an embodiment of an elbow attachment mounting for a flexure measurement device.

Referring to FIG. 10, a schematic pictorial diagram illustrates an embodiment of an elbow attachment mounting 1000 for a flexure measurement device 1002. The elbow attachment mounting 1000 includes a mesh tube 1004 that is positioned by sliding the tube up the arm. The flexure measurement device 1002 is positioned lateral to the elbow so that flexion and extension of the elbow are measured.

While the invention has been described with reference to various embodiments, it will be understood that these embodiments are illustrative and that the scope of the invention is not limited to them. Many variations, modifications, additions and improvements of the embodiments described are possible. For example, those skilled in the art will readily implement the steps necessary to provide the structures and methods disclosed herein, and will understand that the process parameters, materials, and dimensions are given by way of example only and can be varied to achieve the desired structure as well as modifications which are within the scope of the invention. Variations and modifications of the embodiments disclosed herein may be made based on the description set forth herein, without departing from the scope and spirit of the invention as set forth in the following claims.

For example, the exercise or rehabilitation therapy system is described for applications of managed care organizations, hospitals, orthopedic practices, sports medicine practices, rehabilitation centers, and physical therapy clinics. In alternative embodiments, such as simplified embodiments, an exercise system is applied for usage in non-medical markets including rigorous, professional, sport-specific, conditioning, training, and coaching markets.

What is claimed is:

1. A flexure measurement device comprising:
   a flexible member with a single degree of freedom;
   two rigid members attached to opposite ends of said flexible member; and
   a device for determining and displaying the angle between said rigid members, comprising:
      a single wire always positioned a fixed distance from said flexible member, said single wire threaded through blocks attached to said flexible member;
      a light source attached to one end of said single wire;
      a digital array light sensor positioned so as to be capable of detaching movement of the light but at no time in electrical contact with said flexible member, said rigid members, said single wire, or said light source;
      electronics attached to said digital array light sensor for calculating the angle between said rigid members by using a scale and offset, said scale and said offset being configurable by a user of the invention; and
      a digital read out attached to said electronics for displaying of the angle between said rigid members.

* * * * *